United States Patent [19]

Percy et al.

[11] 4,135,142
[45] Jan. 16, 1979

[54] NON-LINEAR ACOUSTIC TRANSDUCER

[75] Inventors: Joseph L. Percy; Ludwig R. Duykers, both of San Diego, Calif.

[73] Assignee: The United States of America as represented by the Secretary of the Navy, Washington, D.C.

[21] Appl. No.: 822,475

[22] Filed: Aug. 8, 1977

[51] Int. Cl.² .......................................... H04B 13/00
[52] U.S. Cl. ................................. 340/8 R; 340/8 LF
[58] Field of Search .................. 340/8 R, 8 PC, 8 LF, 340/8 FT, 8 N, 9, 10, 11, 12 R, 13; 181/106, 113, 119, 120; 73/632, 644

[56] References Cited

U.S. PATENT DOCUMENTS

| 1,500,243 | 7/1924 | Hammond, Jr. | 340/12 R |
|---|---|---|---|
| 2,689,947 | 9/1954 | Fry | 340/10 |
| 2,867,802 | 1/1959 | Lindenblad | 340/12 R |
| 2,939,106 | 5/1960 | Mason | 340/10 |
| 3,048,816 | 8/1962 | Lubnow | 340/12 R |
| 3,219,970 | 11/1965 | Sims | 340/8 R |

Primary Examiner—Harold J. Tudor
Attorney, Agent, or Firm—Richard S. Sciascia; Ervin F. Johnston; Thomas Glenn Keough

[57] ABSTRACT

An improvement for a transducer provides an improved operational characteristic for the transmission and reception of acoustic energy in a liquid medium. A rigid shell having an open end and a closed end is vertically oriented to contain a transducer disposed in a portion of the liquid medium. Inside the shell and in direct contact with the surface of the portion of liquid is a gas filled chamber. The transducer and chamber acoustically cooperate to heterodyne transmitted or received acoustic energy. Difference and sum frequencies optionally are selected for data processing. The frequencies of the heterodyned signals are changed by changing the dimensions of the gas filled chamber. Thus, the relatively small transducer is capable of broadband and low frequency transmission.

8 Claims, 3 Drawing Figures

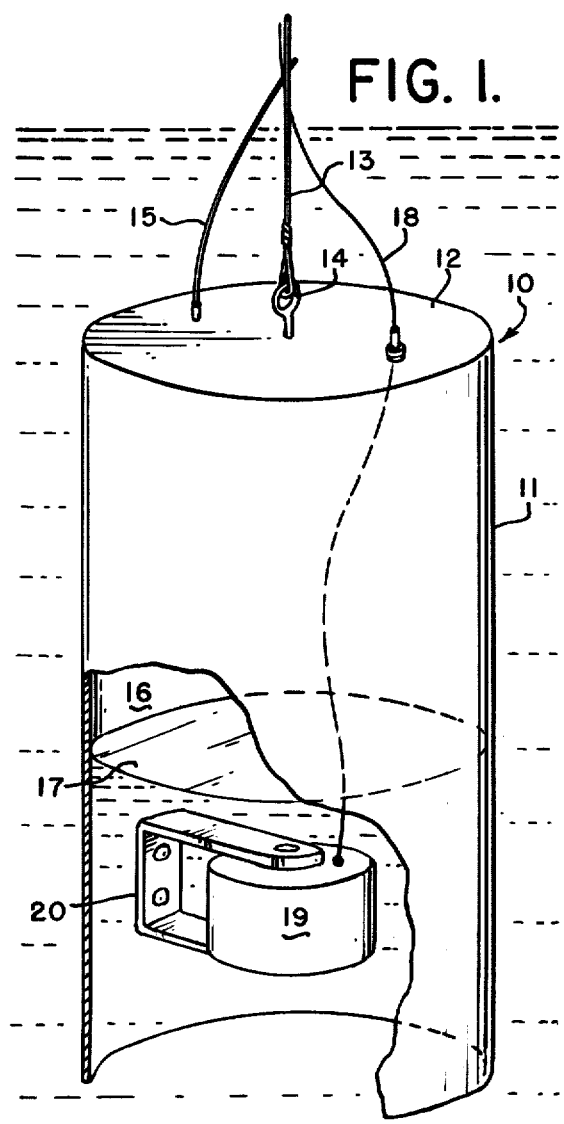
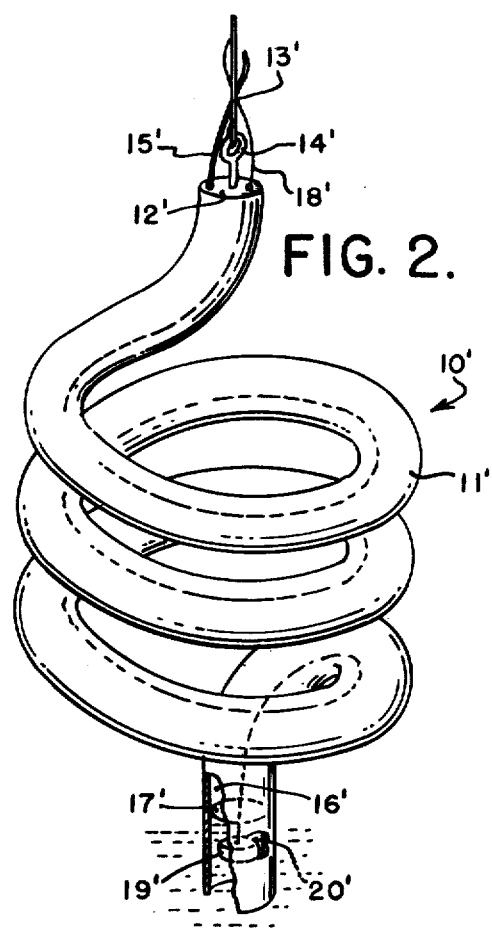
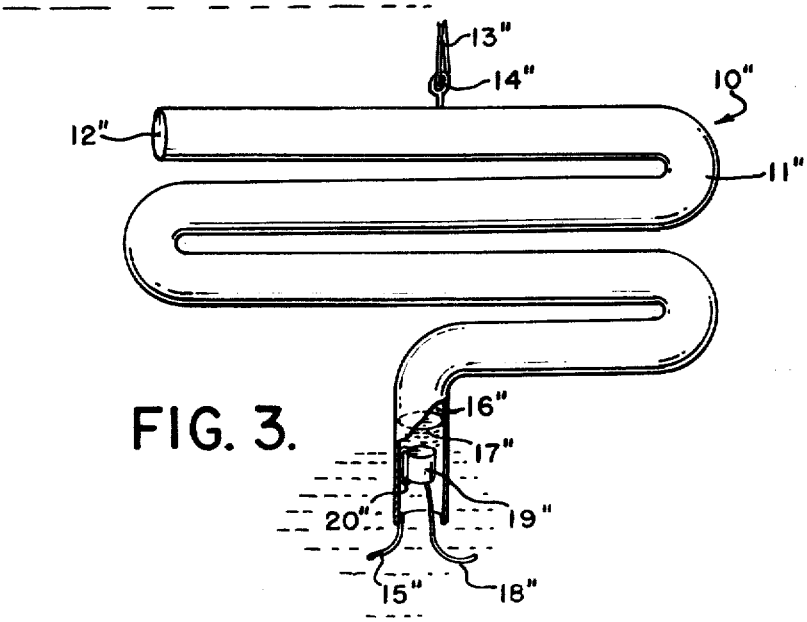

NON-LINEAR ACOUSTIC TRANSDUCER

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

Transducers of acoustic energy in a liquid medium are many and varied in design. The selective projection and reception of acoustic energy over a broad frequency spectrum has been actively pursued with the varying results. Processing low frequency acoustic energy generally has dictated that the dimensions of the transducer be very large since the dimensions of the transducer are preferably in the order of a half wave length of the lowest frequency of interest. Thus, frequencies as low as ten Hz call for having a huge, ponderous transducers that are not only difficult to handle but are expensive. There are a good number of small transducers which exhibit a satisfactory response in the higher frequency ranges but are unable to function satisfactory at lower frequencies. The smaller transducers are more manageable and are not overly expensive. Designers long have sought to use these smaller transducers for low frequency operation but, largely, have been disappointed. In one approach a number of compliant bags are placed in the transducer's proximity or the transducer's housing is enlarged to have internal gas volumes communicating with a projection surface. Both of these approaches call for adding expensive, hard to fabricate or machine structures which boost the price and increase the bulk of the modified transducers. Thus, there is a continuing need in the state-of-the-art for an improvement for a transducer which is not overly expensive and gives a capability for transmitting a broad band of acoustic energy that embraces the lower frequency spectrum.

SUMMARY OF THE INVENTION

The present invention is directed to providing an improvement for an apparatus having a transducer of acoustic energy disposed in a liquid medium. A means defines a rigid shell having an open end and a closed end which is oriented to contain the transducer and a portion of the liquid medium near the open end. The rigid shell of the defining means traps a volume of gas directly in contact with the surface of the portion of the liquid medium whereby heterodyning of discrete frequencies of acoustic energy allows the selected transmission and reception of the sum and difference signals thereof.

An object of the invention is to provide an improvement for a transducer which gives the transducer an extended operating spectrum.

Another object is to provide an improvement for a transducer giving the transducer a low frequency acoustic capability.

Still another object of the invention is to provide an improvement which cooperates with a transducer to heterodyne signals and to optionally transmit or receive sum and difference signals.

Yet another object is to provide an improvement having a variable dimensioned gas filled chamber to alter the response of a transducer.

A further object is to provide an improvement for a transducer having a gas in a chamber directly in contact with a portion of the water medium to improve the transmission characteristics.

Yet another object is to provide an improvement for a transducer being cylindrically shaped to form a cylindrical gas filled chamber.

Another object of the invention is to provide an improvement which is helically shaped to form a helical gas filled chamber.

Yet another object is to provide an improvement which is serpentine shaped to form a serpentine gas filled chamber.

These and other objects of the invention will become more readily apparent from the ensuing description when taken with the drawings.

BRIEF DESCRIPTION OF THE DRAWINGS

FIG. 1 is an isometric depiction of a cylindrically shaped version of the invention.

FIG. 2 is an isometric depiction of a helically shaped version of the invention.

FIG. 3 shows a serpentine version of the invention.

DESCRIPTION OF THE PREFERRED EMBODIMENTS

Referring now to the drawings, an improvement 10 is shown which assures the more responsive transmission and reception of acoustic energy through a liquid medium. A cylindrically shaped shell 11 is closed at one end by a disk 12 and its opposite end is left open. The shell and disk are fabricated from a rigid metal or plastic shell. The exact building material chosen is not overly critical but it should be one that is noncorrosive or corrosion resistant to the liquid medium.

The shell is normally vertically oriented when it is suspended by a line 13 reaching through a pad eye 14 connected on the upper surface of a disk-shaped top 12. When the improvement is so suspended, a pressurized air line 15 reaching through a fitting in the disk-shaped top feeds pressurized gas into a chamber 16. The chamber is formed within the inner walls of a portion of shell 11, the inner surface of the disk-shaped top 12 and upper surface 17 of the portion of the ambient water which is contained within the shell. An electrical conductor 18 passes through a fitting in the disk-shaped top, through the chamber and is coupled to acoustic energy transducer 19. The transducer is disposed in a portion of the water which is contained in the shell and, optionally, is mounted on the shell by a bracket 20.

A modification is depicted in FIG. 2 which shows a helically shaped improvement 10'. A helically extending shell 11' has a disk-shaped top 12' at one end and its opposite end is open. When the shell is suspended by a cable 13' coupled to a pad eye 14', a chamber 16' is formed when pressurized gas is fed to it via a line 15'. The dimensions of the chamber are defined by the inner surfaces of the helically extending shell 11', the inner surface of the disk shaped top 12' and upper surface 17' of the liquid which is contained in the lower part of the shell.

An electrical conductor 18' passes the signals representive of acoustic energy to and from a transducer 19'. Like the first embodiment, a bracket 20' is mounted on a portion of shell 11' to hold the transducer below the surface of the portion of the shell contained liquid in the shell.

Another variation is depicted in FIG. 3 which shows a serpentine-shaped shell structure 10" disposed in the liquid medium. One end of the serpentine-shaped shell is closed by a disk 12" while its opposite end is opened. When a line 13" is looped through a pad eye 14" and serpentine-shaped shell is suspended in the liquid, a serpentine-shaped chamber 16" is formed when pressurized gas is introduced via line 15". The volume and the dimensions of the serpentine shaped chamber are determined by the inner surfaces of the serpentine shaped shell 11", the inner surface of top portion 12" and the surface 17" of the portion of the ambient water contained in the lower part of the shell.

An electrical conductor 18" transmits signals to and from a transducer of acoustic energy 19". Like the other embodiments a bracket 20" locates the transducer in that portion of the ambient liquid which has entered the serpentine shaped shell.

It is a well established fact that a gas volume ensonified at its resonant frequency acts as a nonlinear device. This is in direct contrast to conventional parametric transducers which employ the nonlinearity of the medium, usually seawater. However, the resonance attributed to the gas volume is higher in magnitude since the surrounding liquid medium is almost incompressible and is not able to change volume as rapidly as the gas volume. As a result, finite amplitude waves are propagated in a nonlinear fashion. From exhaustive experiments and tests it was found that the gas volume resonance is more intense when the gas volume is in direct contact with the transmitting liquid medium. Thus, the three aforedescribed embodiments of the invention have at least one side of the gas volume on, gas chamber 16, 16' or 16", directly in contact with the liquid medium. This ensures a more efficient energy transmission than through any wall no matter how thin the wall material is.

The resonance of the chambers in either of the embodiments of FIGS. 1, 2, or 3 are computed in accordance with long established open end pipe resonance mathematics. Simply stated, the resonant frequency roughly is equal to the speed of sound through the medium divided by four times the length of the chamber.

A thorough analysis of the resonant frequency phenomenon as it applies to open ended pipes is set forth in the Second Edition of Fundamentals of Acoustics by Kinsler and Frey, John Wiley and Sons Inc., New York, 1962.

Thus, by pumping in or evacuating gas from the gas chambers 16, 16' or 16" via lines 15, 15' or 15" the resonant frequencies are changed at will. It is immediately apparent that the configurations of FIG. 2 and FIG. 3 are capable of much lower resonant frequencies than that of FIG. 1 without being unduly bulky.

Since the resonant frequency is a function of the chambers' lengths, these resonant frequencies are varied in accordance with the dimensions of chambers 16, 16' and 16". When the resonant frequency is determined to be 1000 Hz, the length of rigid shell 11, 11' or 11" in which the chamber is contained is 2.5 feet. Similarly for a 100 Hz resonance a 25 foot chamber length is in order. At 50 Hz a 50 foot length chamber is called for and at 10 Hz a 250 foot length chamber is required. For the lower frequency ranges the helical configuration of FIG. 2 and the serpentine configuration of FIG. 3 are more suitable since these folded shapes greatly reduce the overall lengthes and, hence, make these designs more manageable.

There is another important advantage of having the resonant chambers directly in contact with the liquid's surface near a submerged transducer. Acoustic cooperation between the chamber and the transducer disposed in the water allows a heterodyning of sum and difference frequencies. First, the dimensions of the chamber are fixed at a particular resonant frequency, for example, 100 Hz. When the transducer functions as a projector of acoustic energy, it is driven at frequencies $f_1$ and $f_2$. $f_1$ can be 75 Hz and $f_2$ 25 Hz so that their sum is 100 Hz (the resonant frequency of the chamber). Alternatively, the frequency $f_1$ could equal 900 Hz and $f_2$ could equal 800 Hz so that their difference frequency equals 100 Hz (again, the resonant frequency of the chamber). When a resonant frequency of 10 Hz calls for a 250 foot length chamber, heterodyning $f_1$ of 900 Hz and $f_2$ of 890 Hz will create a difference signal of 10 Hz. It is apparent that a small transducer 19, 19' or 19" can be driven within its normal operating spectrum to create a low frequency difference signal which would otherwise be far below its effective operating range.

Heterodyning by the transducer-chamber combination also gives an improved hydrophone capability. If a frequency of interest is, say, 10 Hz then the chamber is configured with a sufficient length to resonate at say 100 Hz and a transducer is driven at 90 Hz or 110 Hz and the sum or difference of the interest frequency and the transducer frequency will cause the chamber to resonate. The frequency of interest can thus be detected at the higher frequency.

Thus, it is apparent from the foregoing that a capability exists for an extended broad band operation, particularly in the lower frequency spectrums. This capability gives designers a flexibility to use existing, relatively inexpensive, small transducers in conjunction with this improvement to substantially increase the available spectrum and to effectively operate in the lower ranges. The increased capabilities are realized with little or no modifications to the transducers and provide a synergistic product of the cylindrical, helical or serpentine shaped rigid members each containing a gas chamber and a transducer immersed in the liquid medium.

A test of a cylindrical shell as shown in FIG. 1 having a resonant frequency $f_o$ at 27 Hz gave the following results. When the ratio of a varied frequency with respect to the resonant frequency had values of 1.4, 4, 7, 38.1 and 384.1, the efficiency, the difference in dB between the largest received pressure of the varied frequency and the resonant frequency had values of 1.3, −18.4, −36.9 and −44.0dB respectively. A measure of the difference of the received pressure level in dB of the resonant frequency with and without the resonant chamber was 36.5, 21.5, 10.5 and 5.5dB respectively for the above named ratios.

Obviously, many modifications and variations of the present invention are possible in the light of the above teachings, and, it is therefore understood that within the scope of the disclosed inventive concept, the invention may be practiced otherwise than as specifically described.

What is claimed is:

1. An apparatus employing a transducer of acoustic energy for projecting and receiving heterodyned signals through a water medium comprising:

means for defining a rigid shell having an open end and a closed end, the defining means being oriented to contain a portion of the water medium near the open end and to trap a predetermined volume of gas defining a resonant chamber directly in contact with the surface of the portion of the water medium and means coupled to the defining means positioning the transducer in the portion of the water medium near the open end for ensuring the hetrodyning of acoustic energy and for efficiently transmitting and receiving sum and difference signals to and from the water medium.

2. An improved apparatus according to claim 1 in which the trapped gas volume is in a resonant chamber formed by surfaces of the rigid shell, closed end and upper surface of the portion of the water medium contained near the open end.

3. An improved apparatus according to claim 2 in which heterodyning of discrete frequencies occurs in the defining means by the acoustic cooperation between the transducer disposed in the portion of the water medium near the open end and the dimensions of the trapped gas volume for the projection and reception of acoustic energy.

4. An improved apparatus according to claim 3 further including:

means coupled to the defining means for changing the trapped gas volume to thereby project and receive different frequencies of the acoustic energy.

5. An improved apparatus according to claim 4 further including:

means connected to the defining means for suspending it in a vertical orientation to thereby assure trapping the gas volume in contact with the closed end.

6. An improved apparatus according to claim 5 in which the defining means is cylindrically shaped.

7. An improved apparatus according to claim 5 in which the defining means is helically shaped.

8. An improved apparatus according to claim 5 in which the defining means is serpentine shaped.

* * * * *